United States Patent [19]

Kompfner et al.

[11] 4,012,950
[45] Mar. 22, 1977

[54] METHOD OF AND APPARATUS FOR ACOUSTIC IMAGING

[75] Inventors: Rudolf Kompfner, Stanford; Marvin Chodorow, Menlo Park; Ross A. Lemons, Mountain View, all of Calif.

[73] Assignee: The Board of Trustees of the Leland Stanford University, Stanford, Calif.

[22] Filed: Dec. 12, 1974

[21] Appl. No.: 531,902

[52] U.S. Cl. .......................................... 73/67.5 R
[51] Int. Cl.² ....................................... G01N 29/04
[58] Field of Search ............. 73/67.5 R, 67.6, 67.7, 73/67.8 R, 67.8 S, 67.9, 67.5 H; 340/5 MP

[56] References Cited

UNITED STATES PATENTS

| | | | |
|---|---|---|---|
| 2,932,189 | 4/1960 | Carlin | 73/67.7 |
| 3,024,644 | 3/1962 | Fry | 73/67.5 R |
| 3,529,465 | 9/1970 | Kleesattel et al. | 73/67.7 X |
| 3,564,904 | 2/1971 | Brenden et al. | 73/67.5 H |
| 3,587,298 | 6/1971 | Jacobs | 73/67.6 |
| 3,662,589 | 5/1972 | Adler et al. | 73/67.8 |
| 3,774,717 | 11/1973 | Chodorow | 73/67.7 X |
| 3,832,888 | 9/1974 | Langlois | 73/67.5 H |
| 3,898,840 | 8/1975 | McElroy | 73/67.9 |

FOREIGN PATENTS OR APPLICATIONS 1,200,378   7/1970   United Kingdom ............ 73/67.5 R

OTHER PUBLICATIONS

R. A. Lemons et al., Acoustic Microscope–Scanning Version, Applied Physics Letters, vol. 24, No. 5, Feb. 1975, pp. 163–165.

*Primary Examiner*—Richard C. Queisser
*Assistant Examiner*—John P. Beauchamp
*Attorney, Agent, or Firm*—Flehr, Hohbach, Test, Albritton & Herbert

[57] ABSTRACT

A method of and apparatus for imaging objects utilizing acoustic waves wherein an acoustic beam or beams are generated at one or more frequencies and are focused into proximity with the object to generate output acoustic energy at a different frequency or frequencies resultant from nonlinear interactions with the resultant production, after detection and conversion to electric output signals, of high resolution, enhanced images.

38 Claims, 4 Drawing Figures

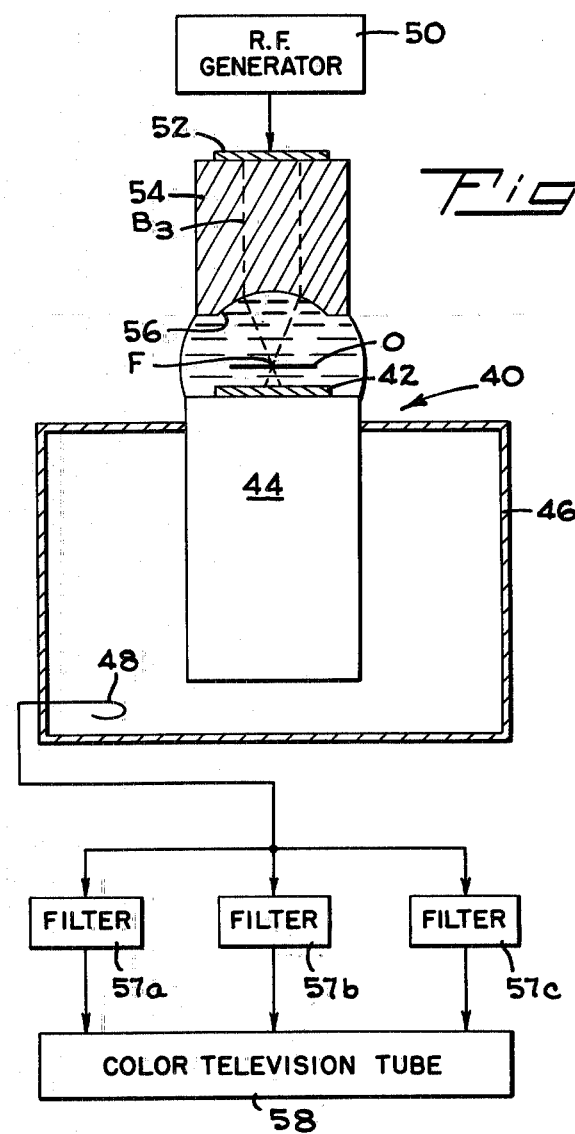
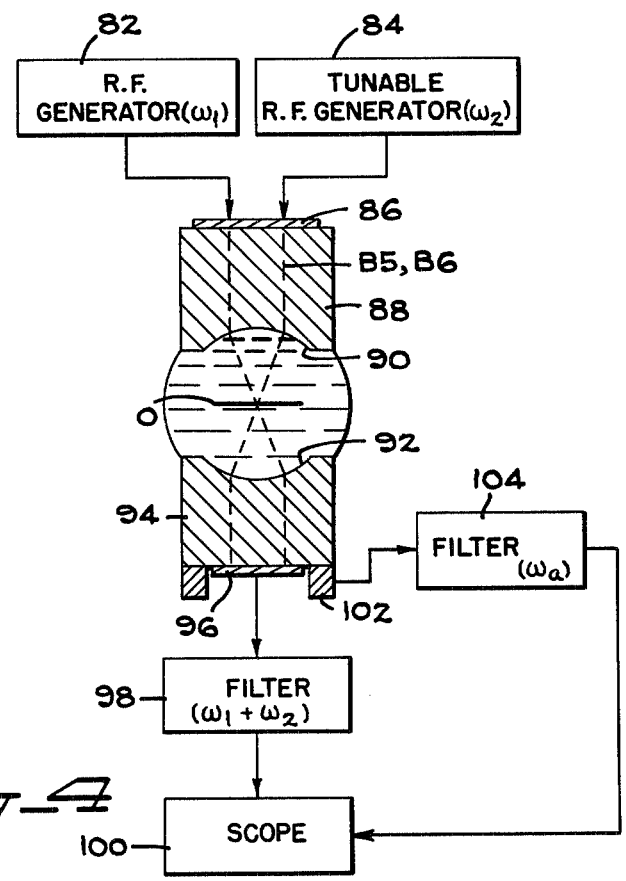

METHOD OF AND APPARATUS FOR ACOUSTIC IMAGING

This invention was made in the course of work performed under a contract/grant by the U.S. Navy.

FIELD OF THE INVENTION

The present invention relates generally to microscopes and other object imaging devices, and more particularly, to a method of and apparatus for the imaging of objects utilizing acoustic waves.

BACKGROUND OF THE INVENTION

Conventional microscopes are based on two forms of radiation, electromagnetic waves as in the optical instruments and the electron waves as in electron microscopes.

Optical instruments have been refined over a period of many years to provide accurate images of even objects as small as biological cells. Regardless of such refinements, inherent limitations exist since the optical systems basically sense the dielectric properties of the specimen or object being imaged. Because of this, certain objects are optically transparent so that no image may be developed while others are optically opaque so that interior details are unrevealed. Furthermore, there are limitations in contrast sensitivity since, for example, there is little intrinsic optical contrast in certain biological specimens such as tissue sections and cell suspensions. Such contrast limitations have been but partially overcome by the very tedious technique of staining biological specimens.

The electron microscope of course is technically much more difficult to construct and use. Additionally, certain objects such as living cells cannot be examined because of the requirements for support in a vacuum and the electron bombardment which damage the cells.

The relatively recent development of acoustic wave generation at frequencies approximating 1,000 MHz provides an acoustic wavelength in water in the neighborhood of one micron and accordingly has suggested itself as a potentially excellent mechanism for the generation of high resolution images. Furthermore, it is the variation in the elastic rather than the dielectric properties of the specimen that determines the scattering, reflection, and absorption of the acoustic energy. This enables the study of details lying beneath the surface of certain specimens which would otherwise be unrevealed due to optical or electron opacity. Furthermore, and of the greatest importance, variations in the elastic properties also show different details, and, in particular, provide for large intrinsic acoustic contrast. As an example, in the Feb. 15, 1974, issue of APPLIED PHYSICS LETTERS an "Acoustic Microscope, Scanning Version" is described in an article appearing on pages 163ff as authored by Lemons and Quate, and as is pointed out has provided good resolution and sensitivity. Briefly, the nature of the object to be imaged is explored by the amount of perturbation or attenuation it offers the acoustic beam or by the reflections or phase shifts caused by changes in acoustical impedance across the object. Practical limitations in the resolution are of course imposed by the operating frequency and the resultant image, of course, is dependent upon the linear elastic properties of the object.

SUMMARY OF THE PRESENT INVENTION

Accordingly, it is the general objective of the present invention to provide a method of and apparatus for acoustic imaging which utilizes the nonlinear interaction of acoustic energy with the object or adjacent medium which generates acoustic energy at a different frequency from that of the input to provide an output signal which is enhanced in its resolution and discloses details of the object not otherwise attainable.

Generally such objective is achieved by an acoustic imaging method which involves as a first step, the generation of one or more radio frequency signals which may be in the microwave frequency region and the subsequent delivery of such signal or signals to a piezoelectric transducer which generates bulk acoustic waves of short wavelength in the form of a collimated beam in an acoustic propagating medium. Each acoustic beam is then delivered to an acoustic lens which effects a sharp convergence of the beam to a focal point whereat the object to be imaged is positioned. A nonlinear interaction of the impinging acoustic energy occurs either within the object itself or in the adjacent medium so as to generate frequencies which are different from those applied and this output acoustic energy is subsequently detected, converted into an electric signal, and delivered to an oscilloscope or other display mechanism whereat an optical image of the object can be displayed.

The method can be carried out in one simple embodiment with an apparatus similar to that described in the mentioned Lemons-Quate article. Radio frequency energy at a fundamental frequency is delivered through a suitable transducer to an acoustic propagating medium having a lens formed thereon to focus the generated acoustic beam to a focal point whereat the object is located, and because of the high degree of convergence, the intensity of the acoustic energy is sufficient to generate harmonics either within the object itself or within the adjacent medium which, as in the Lemons-Quate structure, constituted water.

It can be shown that if a harmonic is generated in the adjoining medium (e.g. water) or in the object itself, the effective spot size at this harmonic frequency is smaller than the effective spot size of the initially injected frequency, and therefore the resolution is enhanced actually in proportion to the order of the harmonic, as will be explained in detail hereinafter. Additionally, and of yet greater significance, if the harmonic generation takes place within the object itself, various parts of the object will now be imaged by way of the variation of harmonic emission in accordance with variations in their higher order elastic properties which may differ considerably from their fundamental ones. As a consequence, both the improved resolution resultant from the generation of harmonic frequencies and the nonlinear interaction within the object itself ultimately provide images which are enhanced as compared to those generated by detection of the perturbed fundamental as in the mentioned Lemons-Quate article.

While the detection can be performed with a structure such as shown in the Lemons-Quate article, including a second spherical output lens which regenerates a collimated acoustic beam which can be detected by a suitable transducer, it will be recognized that since the attenuation losses of the acoustic energy increase with the operating frequency, a slight alternative embodiment of the invention can employ a planar acoustic transducer located immediately beyond the object so that attenuation losses are minimized, the operation being otherwise similar.

As yet another slight modification also arranged to reduce attenuation losses, a reflective type instrument is envisioned wherein the different frequencies (e.g. harmonics), are generated and are immediately thereafter reflected to a suitably disposed output transducer tuned to the different frequency.

In accordance with an additional aspect of the invention, it being recognized that different frequency outputs create different images, it is possible to detect, for example, the fundamental, the second and the third harmonics, and to combine the display of the three outputs on a color oscilloscope which may well provide more easily perceivable characteristics of the object to be imaged.

In addition, it being well known that various materials may have their own mechanical (including molecular) resonances, it is also to be envisioned within the scope of the present invention that several acoustic inputs can be directed to a single object and one can be tuned relative to the other to provide a difference frequency which corresponds to a mechanical resonance of the object, and the effect of this correspondence can ultimately be detected to display additional object characteristics.

BRIEF DESCRIPTION OF THE DRAWINGS

The stated objective of the invention and the manner in which it is achieved, as summarized hereinabove, will be more readily understood by reference to the following detailed description of several specific embodiments of the invention shown in the accompanying drawings wherein:

FIG. 2 is a similar diagrammatic central sectional view of a slightly modified embodiment of the invention, FIG. 4 is yet a further modified embodiment of the invention utilizing multiple input signals arranged to enable interaction with the object at its mechanical resonance frequency.

DETAILED DESCRIPTION OF THE EXEMPLARY EMBODIMENTS OF THE INVENTION

Figure 1:
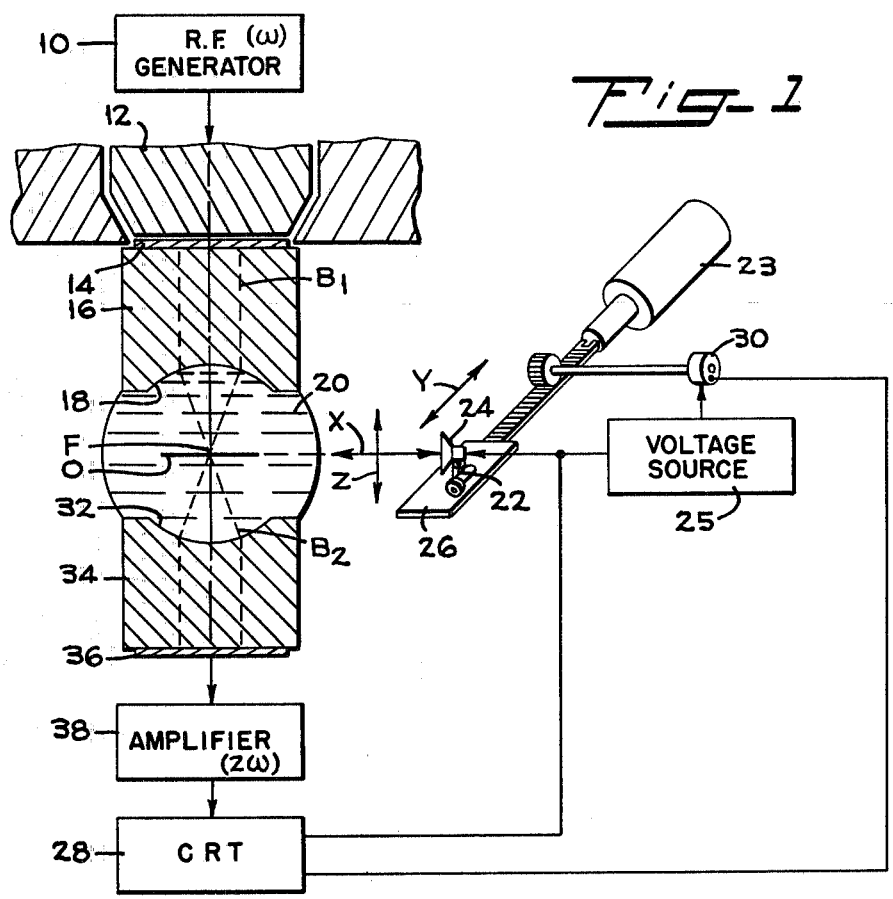
FIG. 1 is a diagrammatic central sectional view of an acoustic imaging apparatus for carrying out the method of the present invention with the associated electronic input and output components illustrated in block diagram form.

With initial reference to FIG. 1, a radio frequency generator 10 is arranged to deliver electromagnetic energy at a frequency ω of, for example, 450 MHz through a coaxial line 12 whose terminal end delivers energy to a thin film or plate piezoelectric transducer 14 at the end of an acoustic propagating medium 16 so as to generate a bulk acoustic wave in the form of a collimated beam indicated at $B_1$.

The transducer 14, in the present instance, can be formed of a thin film of zinc oxide, but other piezoelectric materials such as lithium niobate, cadmium sulphide, zinc sulphide or many other piezoelectric materials can be utilized as is well known to those skilled in the art. In turn, the acoustic propagating medium 16, in the present instance, constitutes sapphire but other acoustic propagating mediums such as fused quartz, yttrium aluminum garnet, a piezoelectric semiconductor such as cadmium sulphide, or other known propagating mediums can be substituted therefor.

An acoustic lens 18 is formed at the extremity of the propagating medium 16 remote from the input transducer 14 and, as specifically illustrated, takes the simple form of a polished concave spherical surface ground into the end of the sapphire material. More particularly, the illustrated lens was ground with a 0.13 millimeter radius of curvature with an $f$ number of 0.75. Accordingly, the collimated acoustic beam $B_1$ is arranged to converge into an adjacent fluid medium 20 which in the present instance constitutes water. Since the water is a slower velocity acoustic medium than the sapphire, the acoustic lens constitutes a positive lens which focuses the beam to a focal point indicated at F.

The object or specimen O to be viewed is supported in the fluid medium 20 close to the focal point F and means are provided to provide for scanning, in the present instance by the simple mechanical motion of the specimen. As diagrammatically indicated in FIG. 1, an adjustable support 22 using a micrometer allows adjustment of the specimen or object O into or out of the focal plane which shall be termed the Z direction. In turn, the focal plane, a fast scan in what is indicated as the X direction in FIG. 1 is provided by mounting on the support 22 a speaker indicated at 24 to whose cone the specimen or object is connected. The support 22, in turn, is mounted on a stage 26 which can be hydraulically reciprocated by a ram 23 in the indicated Y direction. The same voltage that drives the speaker 24 from a source 25 is also delivered to the horizontal deflection control of a conventional cathode ray tube (CRT) or oscilloscope 28 and the reciprocal stage is connected to a potentiometer 30 whose output voltage is delivered to the vertical deflection electrode of the oscilloscope 28 thus providing a one-to-one correspondence between the position of the object and the oscilloscope beam position. As a practical matter, up to a three millimeter field of view with scan rates of 300 lines/second can be achieved so that a complete image can be formed on the oscilloscope in less than one second.

Since the input acoustic lens focuses the primary acoustic beam in a sharply convergent fashion, the acoustic intensity I, at or near the focal point F can be great enough to generate higher acoustic harmonics (e.g. 900 MHz) with detectable amplitude at that position. For illustration, the acoustic intensity of the primary beam as it nears the focal point or its narrow waist can be approximated by a gaussian distribution which drops off from a maximum on the beam axis and can be represented as a function of the radius $r$ from the beam center by $$I_1(r) = I_1 e^{-(r/r_0)^2} \qquad (1)$$

where $r_0$ is the particular radius where intensity drops to a value $1/e$ of the maximum and accordingly represents the spot width of the primary acoustic beam.

In turn, the harmonic intensity generated by the primary beam will have a value described by $$I_n(r) = h_n I_t^n e^{-n(r/r_0)^2} \quad (2)$$

so that an improvement in the resolution of $1/\sqrt{n}$ where $n$ is the order of harmonic, is obtained. $h_n$ is the higher order elastic coefficient of the particular material. In other words, if the initial spot width or effective resolution is represented by the radius $r_0$, the new resolution, $$r_0' = r_{0l} \sqrt{n} \quad (3)$$

Accordingly, if the harmonic generation takes place mainly within the liquid ahead of the object, an acoustic image is obtained at the harmonic frequency based on the local variations of absorption and scattering by the object, but allows an improvement in resolution as indicated by equation (3).

More particularly, if the focal point F is positioned so that the harmonic generation takes place primarily within the object itself, various parts of the object will now be imaged by way of the variation of the harmonic emission (rather than simple perturbation of the primary beam) in accordance with variations in its higher-order elastic properties which may differ considerably from their fundamental ones. Again, in accordance with equation (3), the spot size is reduced at the harmonic frequency so that improved resolution is obtained. As a practical matter, operation at the second harmonic $2\omega$ (900 MHz) has produced images of tissues which differ considerably in their detail as well as resolution as compared to operation at the fundamental frequency.

As shown in FIG. 1, the divergent beam $B_2$ transmitted by the object O is recollimated by another acoustic lens 32 at the end of a sapphire crystal 34 so that the beam impinges upon an output piezoelectric transducer 36 of the same type as the input transducer so that the acoustic signal is detected, converted to an electric signal, and delivered after passage through a conventional band pass amplifier 38 to the gun of the cathode ray tube 28 thus to provide an ultimate optical image which can be directly viewed.

Since the output signal is at a higher (harmonic) frequency, $2\omega$, attenuation losses in the water which are proportional to the square of the frequency and thus increase greatly when a harmonic is generated can be substantial and a slightly modified embodiment of the invention shown in FIG. 2 eliminates the output acoustic lens 32 and substitutes therefor a relatively broad band planar transducer 40 of known design which can be utilized to detect the fundamental and harmonic frequency acoustic signals and to convert them to the corresponding electric output signals. More particularly, the transducer 40 can take the form of a flat layer 42 of zinc oxide or other piezoelectric material supported closely adjacent the object O at the end of a high dielectric constant rod 44, such as rutile, which is disposed in a cavity resonator 46 having an output probe 48 enabling delivery of the output electric signals. Even though the acoustic waves emanating from the object O are not planar since they diverge, the attenuation losses are reduced sufficiently to compensate for phase cancellation in the planar transducer, and it is moreover obvious that precise alignment of such a transducer is not required as is obviously necessary for the output acoustic lens 32 in the FIG. 1 structure.

More particularly, as shown in FIG. 2, a signal from a radio frequency generator 50 is delivered to an input transducer 52 which generates an acoustic beam $B_3$ in a propagating crystal 54 having a convergent acoustic lens 56 formed at its extremity in alignment with the beam as in the described first embodiment of the invention. The beam $B_3$ converges on the object O at its focal point F so that the fundamental frequency acoustic beam is perturbed and harmonics are generated. Both the fundamental and harmonic acoustic signals impinge on the described planar transducer 40.

The output signals from the transducer 40 of the FIG. 2 structure can be delivered to a simple display oscilloscope as in the FIG. 1 structure, but alternatively, as specifically illustrated in FIG. 2, the output signals from the transducer 40 can be delivered simultaneously to three different bandpass filters 57a, 57b, 57c arranged to pass frequencies at the fundamental, the second and the third harmonics, and these three signals whose electrical characteristics will differ because of the different modes of operation can be delivered after suitable amplification and rectification (not shown) to modulate the guns of a color-television display tube 58. Because the human perception mechanism is based on color, this is then a very powerful technique for detecting the differences in information carried by the various frequencies.

Figure 3:
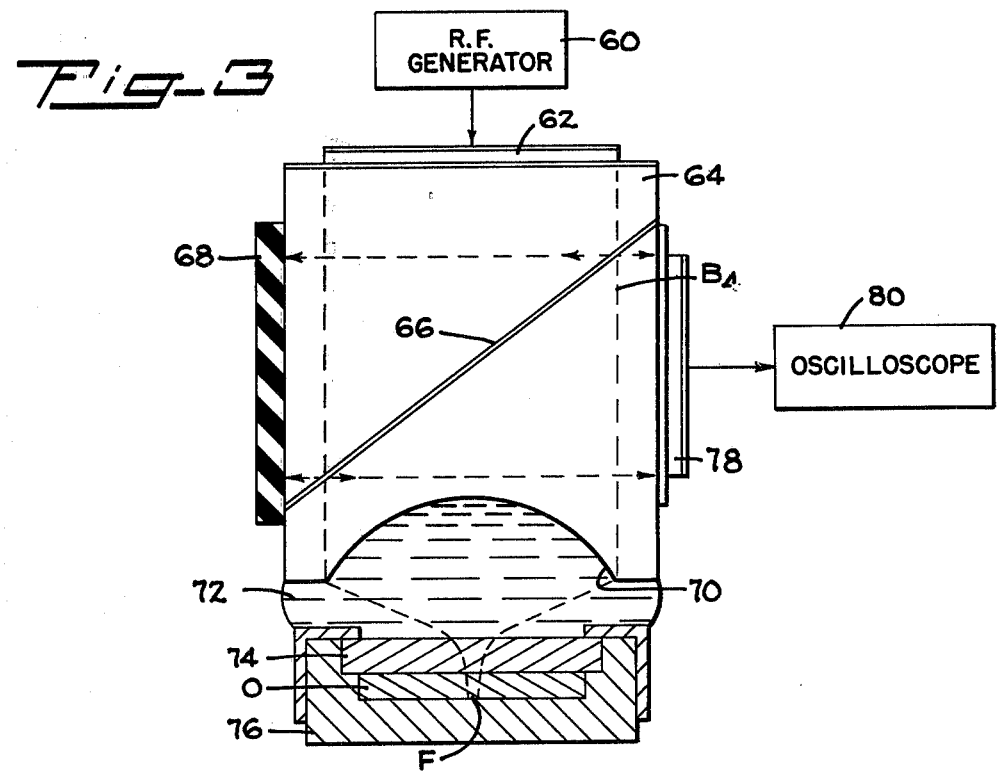
FIG. 3 is yet another central sectional view of a further modified embodiment of the invention wherein reflective acoustic energy is utilized.

The same basic method can obviously be carried out with yet further structures, one constituting a reflective type instrument being illustrated in FIG. 3 wherein an input electrical signal from a suitable radio frequency generator 60 is delivered to an input transducer 62 at one end of a sapphire rod 64 and is to generate an acoustic beam $B_4$. A layer of liquid gallium is placed within the rod 64 at a 45° angle to form a beam splitter 66. A portion of the beam $B_4$ is reflected laterally to be absorbed in an acoustic absorber 68 formed of rubber or other absorptive material but a portion passes on in the same direction and is subsequently focused by an acoustic lens 70 much in the fashion of the first two embodiments of the invention. The convergent acoustic beam $B_4$ is focused through water or a lower loss liquid such as gallium 72 and a low loss solid substrate 74, such as bismuth germanium oxide, to a focal point F adjacent or within the object O which is disposed above a plane acoustic reflector 76 composed of sapphire or gold so that the generated second or third harmonic acoustic energy is directed back through the same lens 70 and thereafter a portion is reflected within the rod 64 laterally by the beam splitter 66 for delivery to an output transducer 78 for subsequent display of the electric output on an oscilloscope 80 much in the fashion of the other embodiments of the invention.

It is also generally known that many substances have mechanical (including molecular) resonances, which typically exist in the frequency range of 10 KHz – 100 MHz and the principles of the present invention can be utilized to excite these resonances of the substance and produce sum or difference frequencies. As best illustrated in FIG. 4, two radio frequency generators 82, 84 at frequencies $\omega_1$ and $\omega_2$ are arranged to generate simultaneous and coincident acoustic beams $B_5$, $B_6$ in a single transducer 86 attached to a sapphire crystal 88 much in the fashion described in more detail in connection with FIG. 1.

As a consequence when the two acoustic beams $B_5$, $B_6$ are both focused into proximity with the object O, by a lens 90, they generate new acoustic frequencies at the difference frequency, $\omega_a = \omega_1 - \omega_2$ and at the sum frequency, $\omega_1 + \omega_2 = \omega_2 + \omega_2 + \omega_a = 2\omega_1 - \omega_a$.

One of the radio frequency generators 82, 84 can be tunable and if tuned so that the difference frequency $\omega_a$ is at or close to a mechanical resonance frequency, the output at the difference frequency will obviously be changed, and correlated changes in the amplitudes of signals at the original and sum frequencies will also occur.

Obviously, the sum frequency will be close to the second harmonic of $\omega_1$ since $\omega_a$ is typically much smaller than either $\omega_1$ or $\omega_2$ and can conveniently be directed by a second acoustic lens 92 in a sapphire rod 94 to an acousto-electric output transducer 96 designed to operate in the region of the second harmonic. The detected and converted output electrical signal can be delivered to an electrical filter 98 which can be used to separate the wanted sum frequency component from the second harmonic and the resulting signal then, after suitable amplification and rectification, can be displayed in the usual manner on an oscilloscope 100. It should be pointed out that even though the mechanical resonance is at a relatively low frequency, the excellent resolution resultant from operation at the harmonic as in the other embodiments of the invention is still achieved.

As an operational alternative, the output signal at one input frequency $\omega_1$ can be detected as one varies the other input signal frequency $\omega_2$, thus to provide an observable change in output signal amplitude when one or more mechanical resonances are encountered.

A simple addition of a low frequency transducer 102 as indicated by a piezoelectric ring of appropriate dimensions on the edge of the sapphire crystal can be utilized to detect and convert acoustic energy at the difference frequency, $\omega_a$ for delivery through a filter 104 to the oscilloscope 100.

It is obvious that many other modifications and/or alterations in the structures as described can be envisioned within the general scope of the spirit of the invention, and accordingly, the description of several embodiments is not to be considered in a limiting sense and the actual scope of the invention is to be indicated only by reference to the appended claims.

What is claimed is:

1. The method of acoustic imaging an object which comprises the steps of generating an acoustic beam at a predetermined frequency, focusing the acoustic beam at a predetermined focal point located in proximity to the object to be imaged whereby the focused acoustic energy impinges on the object, detecting acoustic energy resultant from such impingement with the object at a different frequency, and converting the detected acoustic energy to an output electric signal.

2. The method of acoustic imaging according to claim 1 wherein
said detecting is performed at a frequency higher than the frequency of the focused acoustic beam.

3. The method of acoustic imaging according to claim 1 wherein
said detecting is performed at a frequency constituting a harmonic of the frequency of the acoustic beam.

4. The method of acoustic imaging according to claim 1 wherein
said detecting is performed in close proximity to the object.

5. The method of acoustic imaging according to claim 1 which comprises the additional steps of
detecting acoustic energy at at least one additional frequency, and
converting the energy to at least one additional and separate output electric signal.

6. Acoustic imaging apparatus which comprises
an acoustic propagating medium,
means forming an acoustic lens with a predetermined focal point at the end of said propagating medium,
means for generating an acoustic beam at a predetermined frequency in said medium directed to said acoustic lens to effect convergence of the acoustic energy to the focal point,
means supporting the object to be imaged in a fluid medium encompassing the focal point, and
means for detecting acoustic energy at a different frequency resultant from interaction of the acoustic beam with said fluid medium or the object itself.

7. Acoustic imaging apparatus according to claim 6 wherein
said detecting means includes a planar piezoelectric transducer in close proximity to said focal point.

8. Acoustic imaging apparatus according to claim 6 which comprises
means for reflecting the acoustic energy resultant from the interaction back to said acoustic lens.

9. Acoustic imaging apparatus according to claim 8 which comprises
a beam splitter in said propagating medium for separating the incident and reflected acoustic energy.

10. The method of claim 1 further including the step of scanning the object in a predetermined pattern with the acoustic beam.

11. A method for acoustic imaging an object, comprising the steps of:
a. propagating acoustic waves in an acoustic wave propagating medium at a predetermined frequency;
b. focusing the acoustic waves on an object located proximate to a predetermined focal point;
c. modulating the acoustic waves with the object;
d. receiving the acoustic waves modulated by the object at a frequency different from said predetermined frequency;
e. providing relative motion between the object and the focal point in a scanning pattern and;
f. displaying an image of the object corresponding to the acoustic waves modulated by and received from the object.

12. The method of claim 11 wherein the step of modulating the acoustic waves with the object includes transmitting acoustic waves through the object.

13. The method of claim 11 wherein the step of modulating the acoustic waves with the object includes reflecting acoustic waves off of the object.

14. The method of claim 11 wherein the step of propagating acoustic waves at a predetermined frequency is performed in the frequency range of between one half of one megahertz and three gigahertz.

15. The method of claim 11 wherein the step of providing relative motion includes moving the object in a scanning pattern with respect to the focal point.

16. The method of claim 11 wherein the step of providing relative motion includes moving the focal point in a scanning pattern with respect to the object.

17. Method of scanning an object with acoustic waves comprising the steps of:
   a. generating acoustic waves at a predetermined frequency in an acoustic propagating medium with a transducer;
   b. focusing the waves with a concave acoustic lens located at one end of the propagating medium;
   c. providing relative motion between the object and the focused acoustic waves in a raster pattern perpendicular to the direction of the focused acoustic waves;
   d. modulating the focused acoustic waves with the relatively moving object;
   e. recollimating the acoustic waves modulated by the object;
   f. detecting the recollimated acoustic waves at a frequency different from said predetermined frequency; and
   g. displaying a picture of said object wherein said picture has an optical density at predetermined locations thereon corresponding to the detected acoustic waves at corresponding locations on said object.

18. The method of claim 17 further including the step of synchronizing the raster pattern of the relative motion of the object with the display of the picture, said display having a corresponding raster.

19. The method of claim 17 wherein the step of providing relative motion includes the step of moving the object in two mutually perpendicular directions that are also perpendicular to the direction of the focused acoustic waves.

20. The method of claim 17 wherein the step of detecting the acoustic waves, includes:
   a. converting the detected acoustic waves into corresponding electrical output signals; and
   b. band-pass-filtering the electrical output signals into a predetermined operating band having frequencies different from the acoustic wave generating frequency.

21. The method of claim 17 wherein the step of detecting is performed at a frequency higher than the predetermined frequency of the focused acoustic beam.

22. The method of claim 17 wherein the step of detecting is performed at a frequency constituting a harmonic of the predetermined frequency of the focused acoustic beam.

23. The apparatus of claim 6 further including means providing relative movement between the apparatus and the object to cause said object to be scanned by the acoustic beam.

24. The apparatus of claim 6 wherein said detecting means includes means for obtaining a visible image of the object.

25. The apparatus of claim 24 wherein said image means includes means to contrast the image corresponding to changes in the detected acoustic energy and in relation to the relative position of said object to said acoustical beam.

26. The apparatus of claim 23 wherein the relative moving means translates said object through the focal point of said lens in two mutually perpendicular directions.

27. The apparatus of claim 23 wherein said relative moving means translates said object in a raster pattern and said detecting means includes a CRT display raster synchronized to the translational movement of said object.

28. The apparatus of claim 23 wherein the relative moving means translates the apparatus with respect to the object.

29. Apparatus for scanning an object with acoustic waves, comprising:
   a. a first acoustic medium wherein acoustic waves are propagated;
   b. first means forming an acoustic lens at the end of said first propagating medium;
   c. means for generating acoustic waves at a predetermined frequency in the first propagating medium, said waves being directed toward the acoustic lens and focused therewith;
   d. a second acoustic medium wherein acoustic waves are recollimated;
   e. second means forming an acoustic lens at the end of said second propagating medium, said first and second acoustic lenses having coincident foci;
   f. transducer means for converting the acoustic waves in the second acoustic medium into electrical signals;
   g. means for filtering the electrical signals from the transducer means to obtain electrical signals having a frequency different from said predetermined frequency;
   h. a fluid medium in fluid contact with both acoustic lenses and the foci of said lenses;
   i. means for providing relative movement between the object and the foci of the lenses so that the object moves relatively in a plane perpendicular to the direction of the acoustic waves and through the foci of the acoustic lenses and so that the object modulates the acoustic waves and the electrical signals from the transducer means converted therefrom; and
   j. means for obtaining a picture of the object wherein the contrast of the picture at predetermined locations corresponds to changes in the electrical signals having a frequency different from the predetermined frequency, said predetermined locations corresponding to the position of the object as determined by the moving means.

30. The apparatus of claim 28 wherein the moving means translates the object through the foci of the acoustic lenses in two mutually perpendicular directions.

31. The apparatus of claim 28 wherein the moving means translates the object in a raster pattern and the picture means includes a CRT display with a raster synchronized with the translation of the object.

32. The apparatus of claim 28 wherein the first and second acoustic media are disposed to reflect acoustic waves from the object and said picture means displays an optical density corresponding to the acoustic energy reflected by the object.

33. A microscope for scanning an object with ultrasonic acoustic waves, comprising:
   a. a first single-surface acoustic lens having a concave spherical surface at one end with a predetermined focal point;
   b. a transmitting transducer attached to the first acoustic lens and generating therein plane acoustic waves having a predetermined frequency;
   c. a second single-surface acoustic lens having a concave spherical surface at one end with a predetermined focal point, said first and second lenses being positioned so that their foci are coincident;

d. a fluid medium in fluid contact with both the acoustic lenses and the foci of said lenses;

e. means providing relative movement between the object and the foci of the lenses so that the object moves relatively in a raster pattern perpendicular to the direction of the acoustic waves and through the foci of the acoustic lenses and so that the object modulates the acoustic beam;

f. a detecting transducer attached to the second acoustic lens for receiving the acoustic waves modulated by the object and recollimated by the second acoustic lens, said transducer having output signals corresponding to the modulation of the acoustic waves by the object;

g. band pass filter means connected to the detecting transducer for obtaining from said output signals corresponding electrical signals having a frequency different from said predetermined frequency; and h. display means having a raster trace synchronized to the raster pattern of the moving means and connected to the band pass filter means so that the electrical signals therefrom produce a visual pattern corresponding to the modulation of the acoustic beam by the object.

34. The apparatus of claim 32 wherein the display means produces a visual pattern having a contrast at predetermined locations corresponding to changes in the intensity of the electrical signals obtained from the band pass filter means, said predetermined locations corresponding to the position of the object as determined by the moving means.

35. The apparatus of claim 32 wherein the display means includes a CRT display and the output signals from the detecting transducer modulate the intensity of the electron beam of said CRT display.

36. The apparatus of claim 32 wherein the band pass filter means provides electrical signals to the display means at a frequency higher than the predetermined frequency of the acoustic waves generated by the transmitting transducer.

37. The apparatus of claim 32 wherein the band pass filter means provides electrical signals to the display means at a frequency constituting a harmonic of the predetermined frequency of the acoustic waves generated by the transmitting transducer.

38. The apparatus of claim 32 wherein the transmitting transducer generates acoustic waves having a frequency of between one half of one megahertz and three gigahertz.

* * * * *